(12) United States Patent
Krasovskiy et al.

(10) Patent No.: US 11,161,091 B2
(45) Date of Patent: Nov. 2, 2021

(54) COMPOSITION FOR ODOR SUPPRESSION

(71) Applicants: Dow Global Technologies LLC, Midland, MI (US); Rohm and Haas Company, Collegeville, PA (US)

(72) Inventors: Arkady L. Krasovskiy, Lake Jackson, TX (US); Kefu Sun, Freeport, TX (US); Keran Lu, Lake Jackson, TX (US); Scott T. Matteucci, Midland, MI (US); Alexander Williamson, Lake Jackson, TX (US); Jose Eduardo Ruiz, Freeport, TX (US); Harpreet Singh, Lake Jackson, TX (US); Michelle Gallagher, Collegeville, PA (US); Jeffrey E. Bonekamp, Midland, MI (US)

(73) Assignees: Dow Global Technologies LLC, Midland, MI (US); Rohm and Haas Company, Collegeville, PA (US)

( * ) Notice: Subject to any disclaimer, the term of this patent is extended or adjusted under 35 U.S.C. 154(b) by 66 days.

(21) Appl. No.: 16/608,985

(22) PCT Filed: Feb. 22, 2019

(86) PCT No.: PCT/US2019/019195
§ 371 (c)(1),
(2) Date: Oct. 28, 2019

(87) PCT Pub. No.: WO2019/168757
PCT Pub. Date: Sep. 6, 2019

(65) Prior Publication Data
US 2020/0055018 A1    Feb. 20, 2020

Related U.S. Application Data

(60) Provisional application No. 62/636,453, filed on Feb. 28, 2018.

(51) Int. Cl.
*B01J 20/06* (2006.01)
*A61L 9/014* (2006.01)
(Continued)

(52) U.S. Cl.
CPC .............. *B01J 20/06* (2013.01); *A61L 9/014* (2013.01); *B01J 20/261* (2013.01);
(Continued)

(58) Field of Classification Search
CPC .............. C08K 3/22; C08K 2003/2296; C08K 2201/003; C08K 2201/006;
(Continued)

(56) References Cited

U.S. PATENT DOCUMENTS 4,757,099 A * 7/1988 Hoshino ................. A61L 9/042
523/102
5,654,061 A * 8/1997 Visioli .................... B01J 20/183
428/34.9
(Continued)

FOREIGN PATENT DOCUMENTS

WO    2012/088213 A1    6/2012
WO    2017/093541 A1    6/2017

*Primary Examiner* — Mark Kopec
*Assistant Examiner* — Jaison P Thomas
(74) *Attorney, Agent, or Firm* — Quarles & Brady LLP

(57) ABSTRACT

The present disclosure provides a composition. In an embodiment, the composition includes (A) from 85 wt % to 99 wt % of an olefin-based polymer and (B) from 15 wt % to 1 wt % of an odor suppressant. The odor suppressant is a blend of (i) particles of zinc oxide, and (ii) zinc ionomer. The zinc oxide particles have a D50 particle size from 100 nm to 3000 nm, a surface area from 1 $m^2/g$ to 9 $m^2/g$, and a porosity less than 0.020 $m^3/g$. The composition has a methyl mercaptan odor suppression value of less than 70 at 3 days as measured in accordance with ASTM D5504-12.

13 Claims, 1 Drawing Sheet

SEM of CS3

(51) Int. Cl.
    *B01J 20/26*     (2006.01)
    *B01J 20/28*     (2006.01)
    *B01J 20/30*     (2006.01)
(52) U.S. Cl.
    CPC ..... *B01J 20/2803* (2013.01); *B01J 20/28004* (2013.01); *B01J 20/28059* (2013.01); *B01J 20/28076* (2013.01); *B01J 20/3042* (2013.01); *A61L 2209/22* (2013.01)
(58) Field of Classification Search
    CPC .. C08L 23/0876; C08L 23/06; C08L 23/0815; A61L 2209/22; A61L 9/014; B01J 20/06; B01J 20/261; B01J 20/28004; B01J 20/2803; B01J 20/28059; B01J 20/28076; B01J 20/3042
    See application file for complete search history.

(56) References Cited

U.S. PATENT DOCUMENTS

| | | |
|---|---|---|
| 5,677,383 A | 10/1997 | Chum et al. |
| 5,750,611 A | 5/1998 | Trouihet |
| 6,111,023 A | 8/2000 | Chum et al. |
| 6,344,525 B1 | 2/2002 | Lee et al. |
| 6,448,335 B1 | 9/2002 | Braga et al. |
| 6,521,553 B1 * | 2/2003 | Tabata ............ A61L 9/01 442/123 |
| 6,984,695 B2 | 1/2006 | Brown et al. |
| 7,241,481 B2 | 7/2007 | Speer et al. |
| 9,108,380 B2 | 8/2015 | Binger et al. |
| 2005/0287318 A1 | 12/2005 | Speer et al. |
| 2009/0067760 A1 | 3/2009 | Shelley et al. |
| 2018/0362232 A1 | 12/2018 | Spigaroli et al. |

* cited by examiner

SEM of CS3

SEM of Example 1

COMPOSITION FOR ODOR SUPPRESSION

BACKGROUND

Many uses of articles made from olefin-based polymer encounter the nuisance of foul odor. Common sources of offending odor include hydrogen sulfide ($H_2S$) emitting compositions and thiol-containing compositions. Many applications exist where it is desirable for an olefin-based polymer article to be able to remove, or otherwise suppress, odor. As such, numerous industries desire materials that can remove sulfur-based odorants such as $H_2S$, mercaptans, and thiols from the gas phase. A common example is the ability of a plastic trash bag liner (i.e., an olefin-based polymer article) to be able to remove odor.

Zinc oxide (ZnO) particles and zinc salts are known to consume many odor-generating molecules such as $H_2S$ and mercaptans. All other factors being equal, it is known that ZnO concentration and odor suppression are directly related—i.e., as ZnO concentration increases in a given olefin-based polymer article, the effectiveness of odor suppression also increases.

Although odor suppression increases as ZnO increases, limits do exist for the amount of ZnO that can be effectively incorporated into olefin-based polymer articles. In the production of blown film trash liners for example, high loading of ZnO particles increases extrusion die lip buildup, thereby causing film defects. High loading of ZnO particles also increases haze resulting in degradation of olefin-based polymer film transparency and/or degradation in film color. High loading of ZnO particles also deleteriously impacts mechanical properties such as impact strength and film tear strength. Processing parameters and end-use mechanical requirements thereby impose practical limits to the load of ZnO particles into olefin-based polymer compositions.

A need therefore exists for olefin-based polymer compositions with improved odor suppression while simultaneously carrying suitable zinc load in order to maintain processability, desired optics, and desired mechanical properties for end-use applications. A need further exists for odor-suppressing articles made from such olefin-based polymer compositions.

SUMMARY

The present disclosure provides a composition. In an embodiment, the composition includes (A) from 85 wt % to 99 wt % of an olefin-based polymer and (B) from 15 wt % to 1 wt % of an odor suppressant. The odor suppressant is a blend of (i) particles of zinc oxide, and (ii) zinc ionomer. The zinc oxide particles have a D50 particle size from 100 nm to 3000 nm, a surface area from 1 $m^2/g$ to 9 $m^2/g$, and a porosity less than 0.020 $m^3/g$. The composition has a methyl mercaptan odor suppression value of less than 70 at 3 days as measured in accordance with ASTM D5504-12.

Definitions

Any reference to the Periodic Table of Elements is that as published by CRC Press, Inc., 1990-1991. Reference to a group of elements in this table is by the new notation for numbering groups.

For purposes of United States patent practice, the contents of any referenced patent, patent application or publication are incorporated by reference in their entirety (or its equivalent U.S. version is so incorporated by reference) especially with respect to the disclosure of definitions (to the extent not inconsistent with any definitions specifically provided in this disclosure) and general knowledge in the art.

The numerical ranges disclosed herein include all values from, and including, the lower and upper value. For ranges containing explicit values (e.g., 1 or 2, or 3 to 5, or 6, or 7), any subrange between any two explicit values is included (e.g., 1 to 2; 2 to 6; 5 to 7; 3 to 7; 5 to 6; etc.).

Unless stated to the contrary, implicit from the context, or customary in the art, all parts and percents are based on weight and all test methods are current as of the filing date of this disclosure.

An "agglomerate" is a plurality of individual fine solid particles clumped or otherwise together forming a single mass.

The terms "blend" or "polymer blend," as used herein, is a blend of two or more polymers. Such a blend may or may not be miscible (not phase separated at molecular level). Such a blend may or may not be phase separated. Such a blend may or may not contain one or more domain configurations, as determined from transmission electron spectroscopy, light scattering, x-ray scattering, and other methods known in the art.

The term "composition" refers to a mixture of materials which comprise the composition, as well as reaction products and decomposition products formed from the materials of the composition.

The terms "comprising," "including," "having" and their derivatives, are not intended to exclude the presence of any additional component, step or procedure, whether or not the same is specifically disclosed. In order to avoid any doubt, all compositions claimed through use of the term "comprising" may include any additional additive, adjuvant, or compound, whether polymeric or otherwise, unless stated to the contrary. In contrast, the term "consisting essentially of" excludes from the scope of any succeeding recitation any other component, step, or procedure, excepting those that are not essential to operability. The term "consisting of" excludes any component, step, or procedure not specifically delineated or listed. The term "or," unless stated otherwise, refers to the listed members individually as well as in any combination. Use of the singular includes use of the plural and vice versa.

An "ethylene-based polymer" is a polymer that contains more than 50 weight percent (wt %) polymerized ethylene monomer (based on the total amount of polymerizable monomers) and, optionally, may contain at least one comonomer. Ethylene-based polymer includes ethylene homopolymer, and ethylene copolymer (meaning units derived from ethylene and one or more comonomers). The terms "ethylene-based polymer" and "polyethylene" may be used interchangeably. Nonlimiting examples of ethylene-based polymer (polyethylene) include low density polyethylene (LDPE) and linear polyethylene. Nonlimiting examples of linear polyethylene include linear low density polyethylene (LLDPE), ultra low density polyethylene (ULDPE), very low density polyethylene (VLDPE), multi-component ethylene-based copolymer (EPE), ethylene/α-olefin multi-block copolymers (also known as olefin block copolymer (OBC)), substantially linear, or linear, plastomers/elastomers, and high density polyethylene (HDPE). Generally, polyethylene may be produced in gas-phase, fluidized bed reactors, liquid phase slurry process reactors, or liquid phase solution process reactors, using a heterogeneous catalyst system, such as Ziegler-Natta catalyst, a homogeneous catalyst system, comprising Group 4 transition metals and ligand structures such as metallocene, non-metallocene metal-centered, heteroaryl, heterovalent aryloxyether, phosphinimine, and others. Combinations of heterogeneous and/or homogeneous catalysts also may be used in either single reactor or dual reactor configurations.

"Ethylene plastomers/elastomers" are substantially linear, or linear, ethylene/α-olefin copolymers containing homogeneous short-chain branching distribution comprising units derived from ethylene and units derived from at least one $C_3$-$C_{10}$ α-olefin comonomer. Ethylene plastomers/elastomers have a density from 0.870 g/cc to 0.917 g/cc. Nonlimiting examples of ethylene plastomers/elastomers include AFFINITY™ plastomers and elastomers (available from The Dow Chemical Company), EXACT™ Plastomers (available from ExxonMobil Chemical), Tafmer™ (available from Mitsui), Nexlene™ (available from SK Chemicals Co.), and Lucene™ (available LG Chem Ltd.).

"High density polyethylene" (or "HDPE") is an ethylene homopolymer or an ethylene/α-olefin copolymer with at least one $C_4$-$C_{10}$ α-olefin comonomer, or $C_4$-$C_8$ α-olefin comonomer and a density from 0.940 g/cc, or 0.945 g/cc, or 0.950 g/cc, 0.953 g/cc to 0.955 g/cc, or 0.960 g/cc, or 0.965 g/cc, or 0.970 g/cc, or 0.975 g/cc, or 0.980 g/cc. The HDPE can be a monomodal copolymer or a multimodal copolymer. A "monomodal ethylene copolymer" is an ethylene/$C_4$-$C_{10}$ α-olefin copolymer that has one distinct peak in a gel permeation chromatography (GPC) showing the molecular weight distribution. A "multimodal ethylene copolymer" is an ethylene/$C_4$-$C_{10}$ α-olefin copolymer that has at least two distinct peaks in a GPC showing the molecular weight distribution. Multimodal includes copolymer having two peaks (bimodal) as well as copolymer having more than two peaks. Nonlimiting examples of HDPE include DOW™ High Density Polyethylene (HDPE) Resins (available from The Dow Chemical Company), ELITE™ Enhanced Polyethylene Resins (available from The Dow Chemical Company), CONTINUUM™ Bimodal Polyethylene Resins (available from The Dow Chemical Company), LUPOLEN™ (available from LyondellBasell), as well as HDPE products from Borealis, Ineos, and ExxonMobil.

An "interpolymer" is a polymer prepared by the polymerization of at least two different monomers. This generic term includes copolymers, usually employed to refer to polymers prepared from two different monomers, and polymers prepared from more than two different monomers, e.g., terpolymers, tetrapolymers, etc.

"Linear low density polyethylene" (or "LLDPE") is a linear ethylene/α-olefin copolymer containing heterogeneous short-chain branching distribution comprising units derived from ethylene and units derived from at least one $C_3$-$C_{10}$ α-olefin, or $C_4$-$C_8$ α-olefin, comonomer. LLDPE is characterized by little, if any, long chain branching, in contrast to conventional LDPE. LLDPE has a density from 0.910 g/cc to less than 0.940 g/cc. Nonlimiting examples of LLDPE include TUFLIN™ linear low density polyethylene resins (available from The Dow Chemical Company), DOWLEX™ polyethylene resins (available from the Dow Chemical Company), and MARLEX™ polyethylene (available from Chevron Phillips).

"Low density polyethylene" (or "LDPE") consists of ethylene homopolymer, or ethylene/α-olefin copolymer comprising at least one $C_3$-$C_{10}$ α-olefin, or $C_4$-$C_8$ α-olefin, that has a density from 0.915 g/cc to less than 0.940 g/cc and contains long chain branching with broad MWD. LDPE is typically produced by way of high pressure free radical polymerization (tubular reactor or autoclave with free radical initiator). Nonlimiting examples of LDPE include Mar-Flex™ (Chevron Phillips), LUPOLEN™ (LyondellBasell), as well as LDPE products from Borealis, Ineos, ExxonMobil, and others.

"Multi-component ethylene-based copolymer" (or "EPE") comprises units derived from ethylene and units derived from at least one $C_3$-$C_{10}$ α-olefin, or $C_4$-$C_8$ α-olefin, comonomer, such as described in patent references U.S. Pat. Nos. 6,111,023; 5,677,383; and 6,984,695. EPE resins have a density from 0.905 g/cc to 0.962 g/cc. Nonlimiting examples of EPE resins include ELITE™ enhanced polyethylene (available from The Dow Chemical Company), ELITE AT™ advanced technology resins (available from The Dow Chemical Company), SURPASS™ Polyethylene (PE) Resins (available from Nova Chemicals), and SMART™ (available from SK Chemicals Co.).

An "olefin-based polymer" or "polyolefin" is a polymer that contains more than 50 weight percent polymerized olefin monomer (based on total amount of polymerizable monomers), and optionally, may contain at least one comonomer. Nonlimiting examples of an olefin-based polymer include ethylene-based polymer or propylene-based polymer.

A "polymer" is a compound prepared by polymerizing monomers, whether of the same or a different type, that in polymerized form provide the multiple and/or repeating "units" or "mer units" that make up a polymer. The generic term polymer thus embraces the term homopolymer, usually employed to refer to polymers prepared from only one type of monomer, and the term copolymer, usually employed to refer to polymers prepared from at least two types of monomers. It also embraces all forms of copolymer, e.g., random, block, etc. The terms "ethylene/α-olefin polymer" and "propylene/α-olefin polymer" are indicative of copolymer as described above prepared from polymerizing ethylene or propylene respectively and one or more additional, polymerizable α-olefin monomer. It is noted that although a polymer is often referred to as being "made of" one or more specified monomers, "based on" a specified monomer or monomer type, "containing" a specified monomer content, or the like, in this context the term "monomer" is understood to be referring to the polymerized remnant of the specified monomer and not to the unpolymerized species. In general, polymers herein are referred to has being based on "units" that are the polymerized form of a corresponding monomer.

A "propylene-based polymer" is a polymer that contains more than 50 weight percent polymerized propylene monomer (based on the total amount of polymerizable monomers) and, optionally, may contain at least one comonomer. Propylene-based polymer includes propylene homopolymer, and propylene copolymer (meaning units derived from propylene and one or more comonomers). The terms "propylene-based polymer" and "polypropylene" may be used interchangeably. Nonlimiting examples of suitable propylene copolymer include propylene impact copolymer and propylene random copolymer.

"Ultra low density polyethylene" (or "ULDPE") and "very low density polyethylene" (or "VLDPE") each is a linear ethylene/α-olefin copolymer containing heterogeneous short-chain branching distribution comprising units derived from ethylene and units derived from at least one $C_3$-$C_{10}$ α-olefin comonomer. ULDPE and VLDPE each has a density from 0.885 g/cc to 0.915 g/cc. Nonlimiting examples of ULDPE and VLDPE include ATTANE™ ultra low density polyethylene resins (available from The Dow Chemical Company) and FLEXOMER™ very low density polyethylene resins (available from The Dow Chemical Company).

Test Methods

D10, D50, and D90 particle size is measured using a Coulter LS 230 Laser Light Scattering Particle Sizer, available from Coulter Corporation. D10 particle size is the particle diameter at which 10% of the powder's mass is composed of particles with a diameter less than this value. D50 particle size is the particle diameter at which 50% of the powder's mass is composed of particles with a diameter less than this value and 50% of the power's mass is composed of particles with a diameter greater than said value. D90 particle size is the particle diameter at which 90% of the powder's mass is composed of particles with a diameter less than this value. Mean volume average particle size is measured using a Coulter LS 230 Laser Light Scattering Particle Sizer, available from Coulter Corporation. Particle size distribution is calculated in accordance with Equation A:

$$\text{Particle size distribution} = \frac{(D90 - D10)}{D50}. \quad \text{Equation A}$$

Dart impact strength is measured in accordance with ASTM D1709, with results reported in grams (g).

Density is measured in accordance with ASTM D792, Method B. The result is recorded in grams per cubic centimeter (g/cc).

Differential Scanning Calorimetry (DSC).

Differential Scanning Calorimetry (DSC) can be used to measure the melting, crystallization, and glass transition behavior of a polymer over a wide range of temperature. For example, the TA Instruments Q1000 DSC, equipped with an RCS (refrigerated cooling system) and an autosampler is used to perform this analysis. During testing, a nitrogen purge gas flow of 50 ml/min is used. Each sample is melt pressed into a thin film at about 175° C.; the melted sample is then air-cooled to room temperature (about 25° C.). A 3-10 mg, 6 mm diameter specimen is extracted from the cooled polymer, weighed, placed in a light aluminum pan (ca 50 mg), and crimped shut. Analysis is then performed to determine its thermal properties.

The thermal behavior of the sample is determined by ramping the sample temperature up and down to create a heat flow versus temperature profile. First, the sample is rapidly heated to 180° C. and held isothermal for 3 minutes in order to remove its thermal history. Next, the sample is cooled to −40° C. at a 10° C./minute cooling rate and held isothermal at −40° C. for 3 minutes. The sample is then heated to 180° C. (this is the "second heat" ramp) at a 10° C./minute heating rate. The cooling and second heating curves are recorded. The cool curve is analyzed by setting baseline endpoints from the beginning of crystallization to −20° C. The heat curve is analyzed by setting baseline endpoints from −20° C. to the end of melt. The values determined are extrapolated onset of melting, Tm, and extrapolated onset of crystallization, Tc. Heat of fusion ($H_f$) (in Joules per gram), and the calculated % crystallinity for polyethylene samples using the following Equation: % Crystallinity=(($H_f$)/292 J/g)×100. Glass transition temperature, Tg, is determined from the DSC heating curve where half the sample has gained the liquid heat capacity as described in Bernhard Wunderlich, *The Basis of Thermal Analysis, in Thermal Characterization of Polymeric Materials* 92, 278-279 (Edith A. Turi ed., 2d ed. 1997). Baselines are drawn from below and above the glass transition region and extrapolated through the Tg region. The temperature at which the sample heat capacity is half-way between these baselines is the Tg.

Elmendorf tear (or tear) is measured in accordance with ASTM D1922-15, machine direction (MD), with results reported in grams-force (gf).

Melt flow rate (MFR) in g/10 min is measured in accordance with ASTM D1238 (230° C./2.16 kg).

Melt index (MI) (12) in g/10 min is measured in accordance with ASTM D1238 (190° C./2.16 kg).

Morphology.

Polymer morphology (and the zinc ionomer/zinc oxide domain size in particular) is determined by way of microscopy utilizing an optical microscope (OM) and a scanning electron microscope (SEM).

A. Sample Preparation

OM and SEM—The films are examined as received and also cryogenically cross sectioned using a diamond knife at −80° C. on a Leica UC7 microtome equipped with an FC7 cryosectioning chamber. Film cross sections of approximately 5 microns in thickness are placed on a glass slide containing immersion oil and covered with a glass cover slip. For SEM examination the cryopolished film cross sections are placed on aluminum sample mounts and sputtered with an Iridium plasma using an Emitech K575X turbo sputter coater for 20 seconds to render samples conductive for scanning electron microscopy.

B. Techniques

OM—An Olympus Vanox research microscope is used under transmitted Nomarski to capture images from cross sections. A Leica MZ-16 stereo microscope is also used under transmitted and reflected illumination. Images are captured using Olympus Stream digital software.

SEM/EDX—An FEI Nano600 scanning electron microscope operated at a 10 kV accelerating voltage to capture secondary and backscatter electron images (SEI and BEI).

Odor Suppression/Odor Suppression Value.

Odor suppression is the ability of a composition to neutralize, or otherwise reduce, the amount of volatile sulfur-containing compounds. In the present disclosure, the odor suppression for methyl mercaptan is measured with two-dimensional gas chromatography coupled with time-of-flight mass spectrometry (GCxGC/TOFMS) in accordance with ASTM D5504-12. A control sample is prepared by placing a film formed from DOWLEX 2085G, ethylene/octene LLDPE, into a Tedlar® bag (polyvinyl fluoride). The Tedlar® bag for the control is subsequently filled with a known amount of methyl mercaptan in a helium gas carrier and the Tedlar® bag is closed. Test samples are prepared by placing a film formed from respective test compositions, each test film placed into a respective Tedlar® bag. Each Tedlar® bag is subsequently filled with a known amount of methyl mercaptan in a helium gas carrier and the Tedlar® bag is closed. GC samples are taken at pre-determined time intervals from each bag in order to evaluate odor suppression capability. An odor suppression value (OSV) is calculated for each test sample by dividing the test sample methyl mercaptan concentration by the LLDPE control methyl mercaptan concentration. The odor suppression value for each test sample is reported as a percentage of methyl mercaptan concentration for the control film.

The odor suppression test is performed as set forth below.

Sample Preparation:

1. Films are formed by cutting 1.0 g of film into strips (approximately 1 cm×30 cm).

2. Each film is inserted into a respective Tedlar® bag, one film per bag. The Tedlar® bag is SKC 1 L sample bag (SKC Tedlar® Sample Bag, 1 Liter, Cat No. 232-01).

3. Unscrew the valve from the Tedlar® bag, insert the film strip into the bag through the valve opening with the handle of a cotton tipped applicator. Install the valve back onto the sample bag, squeeze air out of bag before tightening the valve to seal the bag.

4. The Tedlar® bag is filled with 0.98 L Helium (AirGas, Ultra Grade Helium).

5. Using a gas-tight glass syringe, each helium filled Tedlar® bag is injected with 20 mL of helium gas carrying 1000 ppmv methyl mercaptan.

6. 0.50 mL gas sample is removed from each Tedlar® bag at predetermined time intervals.

7. Each 0.50 mL gas sample is injected into the GCxGC/TOFMS to analyze methyl mercaptan concentration. Gas chromatograph: Agilent Model 6890, equipped with a LECO thermal desorption GCxGC modulator and split injection port, available from Agilent Technologies, 2850 Centerville Road, Wilmington, Del. 19808, or equivalent. Detector: LECO Pegasus Time-of-Flight Mass Spectrometer (TOFMS), available from LECO Corporation, 3000 Lakeview Avenue, Saint Joseph, Mich. 49085, or equivalent. Chromatography data system: LECO ChromaTOF 4D software, available from LECO Corporation, or equivalent. Columns: Primary column: Supelco Petrocol DH, 50 m×0.25 mm ID, 0.50 µm, secondary column: Agilent DB-1701, 1.5 m×0.10 mm ID, 0.10 µm film thickness. The secondary column is in the main GC oven. GCxGC Modulation: Second dimension separation time: 3 sec, hot pulse time: 0.40 sec, cool time between stages: 1.10 sec. Modulator temperature offset: 15° C. above the primary oven. Carrier Gas: Helium, 1.5 mL/min with corrected constant flow via pressure ramps. Inlet: Restek Siltek deactivated 4.0 mm ID Precision Inlet Liner w/Wool, Cat. #21023-213.5, available from Restek, or equivalent. Split injection mode, split ratio: 30:1, temperature: 250° C.

8. Injection volume: 0.50 mL gas sample by a gas-tight glass syringe. Oven Temperature: Primary GC Oven: 40° C., 8 min. Secondary Oven: Off (not in use). LECO TOFMS Detector: Low Mass: 20; High Mass: 150; Acquisition Rate: 100 Hz; Detector Voltage: 1650 Volts; Electron Energy: –70 Volts; Mass detect Mode: Auto; Transfer Line: 250° C.; Ion Source: 200° C.; Solvent Delay: 0 minutes.

9. Odor Suppression Calculation.

Odor suppression=(Concentration gas in sample test bag (sample film) at day X)/(concentration gas in test bag with control film at day X)*100.

A nonlimiting example OSV calculation is provided. At three days the peak area for GC peak area for methylmercaptan in the control sample is 119221, whereas the GC peak area for sample film is 30566 (both in arbitrary units). The odor suppression value for the sample is (30566/119221)*100=57.8. A calibration curve is generated to correlate concentration of methylmercaptan to GC peak area for methylmercaptan. As such, methylmercaptan GC peak area or concentration of methylmercaptan can be used to calculate an odor suppression value, wherein peak areas are compared to peak areas, and concentrations are compared to concentrations.

Porosity and Surface Area.

Brunauer-Emmett-Teller (BET) porosity and surface area analysis are performed using a Micromeritics Accelerated Surface Area & Porosimetry instrument (ASAP 2420). The sample is out-gassed at 105° C. while under vacuum prior to analysis.

The ASAP 2420 instrument employs a static (volumetric) method of dosing samples and measures the quantity of gas that can be physically adsorbed (physisorbed) on a solid at liquid nitrogen temperature. For the multi-point BET measurement the volume of nitrogen uptake is measured at pre-selected relative pressure points at constant temperature. The relative pressure is the ratio of the applied nitrogen pressure to the vapor pressure of nitrogen at the analysis temperature of 77 Kelvin (K). Results for porosity are reported in cubic meters per gram, or $m^3/g$. Results for surface area are reported in square meters per gram, or $m^2/g$.

Zinc-Total Amount.

The total amount of zinc present in a composition is determined with x-ray fluorescence spectrometry (XRS), in accordance with ASTM D6247. Results are reported in parts per million, or ppm.

DETAILED DESCRIPTION

Figure 1:
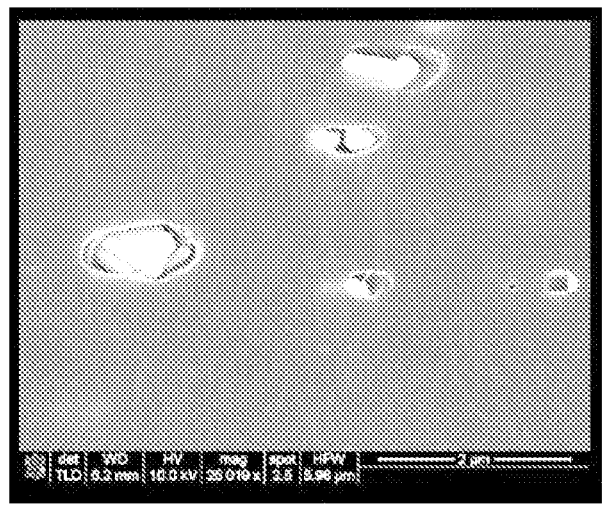
FIG. 1 is a scanning electron microscope (SEM) image of a prior art composition containing a polyethylene with zinc oxide particles dispersed therein.

The present disclosure provides a composition. In an embodiment, a composition for suppressing odors is provided and includes (A) from 85 wt % to 99 wt % of an olefin-based polymer and (B) from 15 wt % to 1 wt % of an odor suppressant. The odor suppressant is a blend composed of (Bi) particles of zinc oxide and (Bii) zinc ionomer. The zinc oxide particles (Bi) have a D50 particle size from 100 nm to 3000 nm, a surface area from 1 $m^2/g$ to 9 $m^2/g$, and a porosity less than 0.020 $m^3/g$. The composition has a methyl mercaptan odor suppression value less than 70 at 3 days exposure to methyl mercaptan as measured in accordance with ASTM D5504-12.

A. Olefin-Based Polymer

The present composition includes an olefin-based polymer. The olefin-based polymer can be a propylene-based polymer or an ethylene-based polymer. Nonlimiting examples of propylene-based polymer include propylene copolymer, propylene homopolymer, and combinations thereof. In an embodiment, the propylene-based polymer is a propylene/α-olefin copolymer. Nonlimiting examples of suitable α-olefins include $C_2$ and $C_4$-$C_{20}$ α-olefins, or $C_4$-$C_{10}$ α-olefins, or $C_4$-$C_8$ α-olefins. Representative α-olefins include ethylene, 1-butene, 1-pentene, 1-hexene, 1-heptene and 1-octene.

In an embodiment, the propylene/α-olefin copolymer is a propylene/ethylene copolymer containing greater than 50 wt % units derived from propylene, or from 51 wt %, or 55 wt %, or 60 wt % to 70 wt %, or 80 wt %, or 90 wt %, or 95 wt %, or 99 wt % units derived from propylene, based on the weight of the propylene/ethylene copolymer. The propylene/ethylene copolymer contains a reciprocal amount of units derived from ethylene, or from less than 50 wt %, or 49 wt %, or 45 wt %, or 40 wt % to 30 wt %, or 20 wt %, or 10 wt %, or 5 wt %, or 1 wt %, or 0 wt % units derived from ethylene, based on the weight of the propylene/ethylene copolymer.

In an embodiment, the olefin-based polymer is an ethylene-based polymer. The ethylene-based polymer can be an ethylene homopolymer or an ethylene/α-olefin copolymer.

In an embodiment, the ethylene-based polymer is an ethylene/α-olefin copolymer. Nonlimiting examples of suitable α-olefins include $C_3$-$C_{20}$ α-olefins, or $C_4$-$C_{10}$ α-olefins, or $C_4$-$C_8$ α-olefins. Representative α-olefins include propylene, 1-butene, 1-pentene, 1-hexene, 1-heptene and 1-octene.

In an embodiment, the ethylene/α-olefin copolymer is an LLDPE that is an ethylene/$C_4$-$C_8$ α-olefin copolymer. The LLDPE has one, some, or all of the following properties:
 (i) a density from 0.910 g/cc to 0.930 g/cc; and/or
 (ii) a Tm from 121° C. to 123° C.; and/or
 (iii) a melt index from 0.5 g/10 min to 1.0 g/10 min.

A nonlimiting example of a suitable LLDPE is DOWLEX 2085 available from The Dow Chemical Company.

B. Odor Suppressant

The present composition includes an odor suppressant. The odor suppressant is a blend of zinc oxide ("ZnO") particles (Bi) and a zinc ionomer (Bii).

B(i) Zinc Oxide

The odor suppressant includes particles of zinc oxide (or "ZnO"). The ZnO particles have a D50 particle size from 100 nm to 3000 nm, a surface area from 1 $m^2$/g to less than 10 $m^2$/g, and a porosity less than 0.020 $m^3$/g.

In an embodiment, the ZnO particles have one, some, or all of the following properties (i)-(iii) below:
 (i) a particle size D50 from 100 nm, or 200 nm, or 300 nm, or 400 nm to 500 nm, or 600 nm, or 700 nm, or 800 nm, or 900 nm, or 1000 nm, or 2000 nm, or 3000 nm; and/or
 (ii) a surface area from 1 $m^2$/g, or 2 $m^2$/g, or 3 $m^2$/g, or 4 $m^2$/g to 5 $m^2$/g, or 6 $m^2$/g, or 7 $m^2$/g, or 8 $m^2$/g, or 9 $m^2$/g; and/or
 (iii) a porosity from 0.005 $m^3$/g, or 0.006 $m^3$/g, or 0.008 $m^3$/g, or 0.010 $m^3$/g to 0.012 $m^3$/g, or 0.013 $m^3$/g, or 0.015 $m^3$/g, or less than 0.020 $m^3$/g.

Nonlimiting examples of suitable ZnO particles include Zochem 102, Zochem 104 from Zochem Inc., and ZnO particles available from US Research Nanoparticles.

B(ii) Zinc Ionomer

The odor suppressant includes a zinc ionomer. The term "zinc ionomer," (or "ZnI/O") as used herein, refers to a copolymer based on a zinc salt of a copolymer of ethylene and a vinyl comonomer with an acid group. Nonlimiting examples of suitable comonomer having vinyl comonomer with an acid group include methyl/methacrylic acid, vinyl acrylic acid, methacrylate, n-butyl acrylic acid, and acrylic acid.

The zinc ionomer is a cross-linked polymer in which the linkages are ionic (i.e., interchain ionic bonding) as well as covalent bonds. The zinc ionomer has positively and negatively charged groups, which are not associated with each other, providing the zinc ionomer with a polar character.

Nonlimiting examples of suitable zinc ionomer include zinc salt of ethylene/acrylic acid comonomer, zinc salt of ethylene/methyl-methacrylic acid copolymer, zinc salt of ethylene/vinyl acrylic acid copolymer, zinc salt of ethylene/methacrylate copolymer, zinc salt of ethylene/n-butyl acrylic acid copolymer, and any combination thereof.

In an embodiment, the zinc ionomer is a zinc salt of ethylene/acrylic acid copolymer. A nonlimiting example of a suitable zinc ionomer is AMPLIFY I/O 3701 available from The Dow Chemical Company.

C. Composition

The present composition includes (A) from 85 wt % to 99 wt % of the olefin-based polymer and (B) from 15 wt % to 1 wt % of the odor suppressant. The odor suppressant is mixed, or otherwise blended into the olefin-based polymer matrix. The odor suppressant is a blend of (Bi) particles of zinc oxide (ZnO) and (Bii) zinc ionomer (ZnI/O). The zinc oxide particles have a D50 particle size from 100 nm to 3000 nm, a surface area from 1 $m^2$/g to 9 $m^2$/g, and a porosity less than 0.020 $m^3$/g and is hereafter referred to as Composition 1. Composition 1 has a methyl mercaptan odor suppression value less than 70 at 3 days exposure to methyl mercaptan.

The odor suppressant is present in an amount from 1 wt % to 15 wt % of Composition 1 (based on total weight of Composition 1), and the ratio of ZnO to ZnI/O (hereafter "ZnO- to ZnI/O ratio") is from 3:1 to 1:7 based on the weight of the odor suppression. The ZnO- to ZnI/O ratio can be from 3:1, or 2:1, or 1:1 to 1:2, or 1:3, or 1:4, or 1:5, or 1:6, or 1:7.

In an embodiment, the present composition includes from 85 wt %, or 90 wt % to 95 wt %, or 97 wt %, or 99 wt % component (A) that is an ethylene-based polymer. The present composition includes a reciprocal amount of component (B), or from 15 wt %, or 10 wt % to 5 wt %, or 3 wt %, or 1 wt % odor suppressant wherein the ZnO- to ZnI/O ratio is from 1:3, or 1:4, or 1:5 to 1:6, or 1:7. The zinc oxide particles (Bi) have a D50 particle size from 100 nm, or 200 nm, or 300 nm, or 400 nm to 500 nm, or 600 nm, or 700 nm, or 800 nm, or 900 nm, or 1000 nm, or 2000 nm, 3000 nm, the zinc oxide particles also have a surface area from 1 $m^2$/g, or 2 $m^2$/g, or 3 $m^2$/g to 4 $m^2$/g, or 5 $m^2$/g, or 6 $m^2$/g, and the zinc oxide particles also have a porosity from 0.0050 $m^3$/g, or 0.0070 $m^3$/g, or 0.0090 $m^3$/g to 0.010 $m^3$/g, or 0.013 $m^3$/g to 0.015 $m^3$/g and is hereafter referred to as Composition 2. Composition 2 has a methyl mercaptan odor suppression value of less than or equal to 55 at 3 days of exposure to methyl mercaptan.

In an embodiment, Composition 2 contains from 1000 ppm, or 5000 ppm, or 10000 ppm, or 20000 to 30000 ppm, or 40000 ppm, or 50000 ppm, or 60000 ppm, or 90000 ppm total zinc. The term "total zinc," as used herein, is the aggregate of zinc metal from the zinc oxide (Bi) and the zinc ionomer (Bii).

In an embodiment, the ethylene-based polymer (A) is present in the composition to the exclusion of any other polymer (with exception of the ZnI/O in the odor suppression). In other words, the ethylene-based polymer is the sole polymeric component (the only polymeric component) in the composition other than the zinc ionomer. In a further embodiment, the sole polymeric component is an LLDPE (other than the zinc inomer).

In an embodiment, the total zinc is present in Composition 2 to the exclusion of International Union of Pure and Applied Chemistry (IUPAC) Group 5 metals to IUPAC Group 12 metals. The term "from Group 5 metals to Group 12 metals," as used herein, includes IUPAC Group 5 metals (Chemical Abstracts Service [CAS] VB), IUPAC Group 6 metals (CAS VIB), IUPAC Group 7 metals (CAS VIIB), IUPAC Group 8 metals (CAS VIIIB), IUPAC Group 9 metals (CAS VIIIB), IUPAC Group 10 metals (CAS VIIIB), IUPAC Group 11 metals (CAS 1B), IUPAC Group 12 metals (CAS IIB). It is understood that zinc is a Group 12 metal, with the exclusion applying to cadmium and mercury. The term "total zinc is present to the exclusion of other Group 5 to Group 12 metals," as used herein, refers to the presence of zinc and the absence of Group 5 to Group 12 metals in the composition, whereby the composition contains from 0 ppm, or from greater than 0 ppm, or 1 ppm, or 2 ppm to 3 ppm Group 5 metal to Group 12 metal.

In an embodiment, Composition 2 is a heterophasic composition and includes a continuous-phase composed of the ethylene-based polymer, component (A) and a discontinuous-phase of component (B). The discontinuous phase is in the form of discrete domains. The domains are composed of the zinc oxide particles embedded in the zinc ionomer. The domains (zinc ionomer with ZnO particles embedded therein) have an average diameter from 500 nm to 1000 nm, or 3000 nm to 5,000 nm, or 7,500 nm, or 10,000 nm as measured in accordance with OM/SEM microscopy.

Applicant discovered Composition 2 having an odor suppressant with ZnO- to ZnI/O ratio from 1:3 to 1:7, ZnO with (i) D50 particle size from 100 nm to 3000 nm (ii) surface area, from 1 m$^2$/g to 6 m$^2$/g, and (iii) porosity from 0.005 m$^3$/g to 0.015 m$^3$/g yields unexpected improvement in odor suppression. The domains are homogeneously dispersed in a continuous phase composed of the ethylene-based polymer.

D. Applications

The present composition may be used in any application wherein a polymeric material, and an olefin-based polymer in particular, is exposed to mercaptans, H$_2$S, disulfides or amines. Nonlimiting examples of suitable applications for the present composition include trash liners, poultry diapers, ostomy bags, mattresses, mattress covers, poultry packaging, automotive interior parts, carpet fibers, and carpet backing.

In an embodiment, the composition is formed into a film. The film includes the present composition, the present composition composed of (A) from 85 wt % to 99 wt % of an olefin-based polymer and (B) from 15 wt % to 1 wt % of the odor suppressant. The odor suppressant is a blend composed of (i) particles of zinc oxide and (ii) a zinc ionomer. The zinc oxide particles have a D50 particle size from 100 nm to 3000 nm, a surface area from 1 m$^2$/g to 9 m$^2$/g, and a porosity less than 0.020 m$^3$/g. The composition has a methyl mercaptan odor suppression value of less than 70 at 3 days as measured in accordance with ASTM D5504-12.

In an embodiment, the film is a blown film formed from Composition 2, Composition 2 having an odor suppressant value less than 70 at 3 days, the blown film having (i) a Dart impact strength from 600 g, or 700 g, or 750 g to 775 g, or 800 g, or 825 g; and/or (ii) an Elmendorf tear strength from 300 gf, or 350 gf, or 375 gf to 400 gf, or 425 gf.

All other factors being equal the more ZnO present in a polymeric composition, the greater the odor suppression capability. ZnO particle surface area and gaseous odor suppression follow a direct correlation whereby the larger the surface area of the ZnO particle, the greater the odor suppression capacity. Similarly, ZnO particle porosity and gaseous odor suppression also follow a direct correlation whereby the greater the porosity of the ZnO particle, the greater the odor suppression capacity.

ZnO load and ZnO particle morphology influence processability and physical properties when present in a polymer matrix. High surface area ZnO particles (i.e., ZnO particles with surface area of 10 m$^2$/g or greater) tend to increase the viscosity of the matrix polymer in which the ZnO particles are embedded, which may degrade polymer melt processing. High surface area ZnO particles also inhibit uniform dispersion of the ZnO particles into a polymeric matrix. Moreover, large ZnO particles (ZnO particles with average diameter greater than 3 microns) added to a polymer matrix are known to degrade polymer film properties. Large ZnO particles are problematic and often act as initiation sites for cracks, tears, and crazing within a polymer matrix, degrading physical properties such as tear strength, elongation, and Dart impact.

Surprisingly, the present composition (i.e., Composition 1 and/or Composition 2) exhibits the same, or better, odor suppression capability without compromising processability and without compromising film properties. Applicant discovered the ZnI/O works synergistically with the ZnO to improve odor suppression with less total zinc (and less ZnO) compared to ZnO-polymer matrix systems containing more ZnO. ZnI/O alone has little, or no, odor suppression capability. The ability of ZnI/O to synergistically improve odor suppression when combined with ZnO particles with D50 100-3000 nm, surface area of 1-9 m$^2$/g and porosity less than 0.02 m$^3$/g is unexpected.

By way of example, and not limitation, some embodiments of the present disclosure will now be described in detail in the following Examples.

EXAMPLES

Materials used in the examples are provided in Table 1 below.

TABLE 1

| Material/Description | Properties | Source |
|---|---|---|
| DOWLEX ™ 2085G (LLDPE) | LLDPE, ethylene/octene copolymer; density = 0.92 g/cc; MI 0.85 g/10 min; Tm = 121.6° C. | The Dow Chemical Company |
| AMPLIFY IO ™ 3701 (ZnI/O) | Metal salt of zinc ion and ethylene/acrylic acid copolymer; density = 0.940 g/cc; Tm = 95° C.; MI = 5.2 g/10 min | The Dow Chemical Company |
| Agility 1021 | LDPE; density = 0.920 g/cc; Tm = 108.1° C.; MI = 1.85 g/10 min | The Dow Chemical Company |
| ZNO 800HSA Zinc Oxide (ZnO-1) powder | ZnO D50 particle size 3000 nm; density = 5.61 g/cc; Porosity 0.0131 g/m$^3$, surface area 4.46 m$^2$/g | Zinc Oxide, LLC |
| Zinc Oxide ZnO MicroPowder, ZnO, 99.9+% Zinc Oxide (ZnO-2) powder | ZnO D50 particle size 500 nm; density = 5.61 g/cc; Porosity 0.008 m$^3$/g, surface area 3.36 m$^2$/g | 500 nm (US Research Nanomaterials) |
| Zoco102 Zinc Oxide (ZnO-3) powder | ZnO D50 particle size 200 nm; density = 5.61 g/cc; Porosity 0.012 m$^3$/g, surface area 4.4 m$^2$/g | Zochem inc. |

TABLE 1-continued

| Material/Description | Properties | Source |
|---|---|---|
| Ampacet 110069 White PE MB Titanium dioxide ($TiO_2$) Masterbatch | 70 wt % $TiO_2$ in Carrier Resin LLDPE (MI 2.3, d-0.917 g/cc) Masterbatch Specific gravity: 2.03 | Ampacet Corporation |

1. Films

The compositions of CS1-CS8 and IE1-IE8 are formed into a blown film by compounding the LLDPE, the ZnO (when present), the ZnI/O (when present), and the $TiO_2$ (when present) in a 30 mm co-rotating, intermeshing Coperion Werner-Pfleiderer ZSK-30 (ZSK-30) twin screw extruder. The extruder is operated at 40 lbs per hour under a screw rotation speed of 250 rpm. Die pressure is maintained between 450 to 500 psi. Melt temperature is maintained near 240° C. Nitrogen purging is applied at the feed throat. A standard water bath is used for cooling and a strand cut pelletizer is employed to product the pellets. Pellets were stored in ambient conditions prior to use.

The blown film is a single layer film.

TABLE 2

Blown film line process parameters

| Parameter | Units | Films without $TiO_2$ MB | Films containing $TiO_2$ MB |
|---|---|---|---|
| Takeoff | m/min | 15 | 15 |
| Layflat | cm | 23.5 | 23.5 |
| Frostline | cm | 14 | 14 |
| B.U.R | ratio | 2.5 | 2.5 |
| Die gap | mm | 2.0 | 2.0 |
| Melt temperature - Ext. A | ° C. | 218 | 218 |
| Melt temperature - Ext. B | ° C. | 226 | 226 |
| Melt temperature - Ext. C | ° C. | 215 | 215 |
| RPM - Ext. A | rpm | 51 | 51 |
| RPM - Ext. B | rpm | 50 | 50 |
| RPM - Ext. C | rpm | 32 | 32 |
| Total Output | kg/hr | 8.8 | 8.8 |
| Film Total Thickness | mm | 0.023 | 0.056 |

In Table 3 below, Dart Impact and tear strength values are for films with 0.023 mm thickness. Films with $TiO_2$ MB have 0.056 mm thickness, with exception to the CS7 film having a thickness of 0.023 mm.

2. Odor Suppression

Odor suppression values are measured over 192 hours (8 days) in accordance with ASTM D 5504-10 as described above in the odor suppression test method.

Film strips with a mass of 1 g (1 cm×30 cm and thickness in Table 2) of control samples (CS) CS1-CS8 and inventive examples (IE) IE1-IE8 are placed in Tedlar® bags filled with methyl mercaptan and helium gas carrier as described in the odor suppression test method, disclosed above.

Comparative samples (CS), CS1-CS8 are prepared. CS1 is a control sample with DOWLEX 2085 and CS2 is a control sample 93 wt % LLDPE and 7 wt % $TiO_2$ masterbatch.

CS3 and CS4 are blends of ZnO and LLDPE (control) with varying amount of ZnO in the blend.

CS5, CS6, CS7 are blends of zinc ionomer and LLDPE (control) with varying amount of zinc ionomer in the blend.

CS8 is a blend of ZnO, $TiO_2$ and LLDPE (control).

IE1-IE8 are inventive examples of the present composition composed of LLDPE and odor suppressant composed of ZnO and ZnI/O.

The odor suppression values (OSV) for CS1-CS8 and IE1-IE8 are provided in Table 3 below.

TABLE 3

Methyl Mercaptan Odor Suppression Values and Blown Film Properties

| Sample | Composition | Day 1 | Day 2 | Day 3 | Day 4 | Day 5 | Day 8 | Tear (gf) | Avg Dart (g) |
|---|---|---|---|---|---|---|---|---|---|
| CS 1 (control) | 7% wt % $TiO_2$ MB 93 wt % LLDPE | 94 | 77 | 94 | 73 | 80 | 89 | 308 | 588 |
| CS 2 (control) | 100% LLDPE 2085 | 100 | 100 | 100 | 100 | 100 | 100 | 337 | 600 |
| CS3 | 5 wt % ZnO-2 (500 nm) 95 wt % LLDPE | 78 | 89 | 81 | 70 | 66 | 68 | 341 | 624 |
| CS4 | 5 wt % ZnO-1 (3000 nm) 95 wt % LLDPE | 82 | 99 | 87 | 66 | 70 | 59 | 403 | 588 |
| CS5 | 10 wt % Zn-I/O 90 wt % LLDPE | 116 | 105 | 114 | 90 | 92 | 117 | 263 | 653 |
| CS6 | 5 wt % Zn-I/O 95 wt % LLDPE | 104 | 102 | 105 | 81 | 88 | 93 | 260 | 683 |
| CS7 | 5 wt % $TiO_2$ MB 5 wt % Zn- I/O 90 wt % LLDPE | 102 | 91 | 92 | 83 | 77 | 89 | 223 | 653 |
| IE1 | 5 wt % ZnO-2 (500 nm) 5 wt % Zn-I/O 90 wt % LLDPE | 37 | 54 | 56 | 47 | 47 | 52 | 337 | 810 |
| IE2 | 5 wt % ZnO-1 (3000 nm) 5 wt % AMPLIFY I/O 3701 90 wt % LLDPE | 72 | 61 | 67 | n/t | n/t | n/t | 420 | 773 |

TABLE 3-continued

Methyl Mercaptan Odor Suppression Values and Blown Film Properties

| Sample | Composition | Day 1 | Day 2 | Day 3 | Day 4 | Day 5 | Day 8 | Tear (gf) | Avg Dart (g) |
|---|---|---|---|---|---|---|---|---|---|
| CS8 | 5 wt % ZnO-3 (200 nm) 5 wt % LDPE 7 wt % TiO₂ MB | 93 | n/t | 93 | n/t | n/t | n/t | | |
| IE3 | 5 wt % ZnO-1 (3000 nm) 5 wt % AMPLIFY IO 7 wt % TiO2 MB | 76 | n/t | 37 | n/t | n/t | n/t | | |
| IE4 | 5 wt % ZnO-2 (200 nm) 5 wt % AMPLIFY IO 7 wt % TiO₂ MB | 68 | n/t | 28 | n/t | n/t | n/t | | |
| IE5 | 1.25 wt % ZnO-3 (200 nm) 1.25 wt % AMPLIFY IO 7% wt % TiO₂ MB | 77 | n/t | 66 | n/t | n/t | n/t | | |
| IE6 | 2.5 wt % ZnO-3 (200 nm) 2.5 wt % AMPLIFY IO 7% wt % TiO₂ MB | 74 | n/t | 54 | n/t | n/t | n/t | | |
| IE7 | 3.75 wt % ZnO-3 (200 nm) 1.25 wt % AMPLIFY IO 7% wt % TiO₂ MB | 95 | n/t | 65 | n/t | n/t | n/t | | |
| IE8 | 1.25 wt % ZnO-3 (200 nm) 3.75 wt % AMPLIFY IO 7 wt % TiO₂ MB | 73 | n/t | 55 | n/t | n/t | n/t | | |

*TiO₂ MB—titanium dioxide masterbatch 70 wt % TiO₂ powder in 30 wt % LLDPE carrier, added for white color
n/t—not tested In Table 3, CS3-CS4 (ZnO only, at 5 wt %) demonstrate that ZnO only at small load (5 wt %) exhibits only a small degree of odor suppression at 3 days (OSV 81, 87 respectively).

CS5-CS6 show ZnI/O only has no ability to suppress odor (114, 105 respective OSV at 3 days).

CS7 shows that with ZnI/O blended with TiO₂ has only a small odor suppression capability (OSV 92 at 3 days).

IE1-IE8 each show significant odor suppression capability (IE1, IE2 OSV 56, 67 respectively at 3 days). For example, the ability of IE1 and IE2 to provide greater odor suppression (respective OSV: 56, 67) than CS4 (OSV: 87) is unexpected. Bounded by no particular theory, the ZnO and ZnI/O work synergistically to improve the odor suppression ability of ZnO. Further unexpected is the discovery that ZnI/O, which alone, is an ineffective odor suppressant, works synergistically with ZnO to improve odor suppression. Applicant discovered that odor suppression improves by blending ZnO with ZnI/O as opposed to increasing only the amount of ZnO in the absence of the zinc ionomer.

Figure 2:
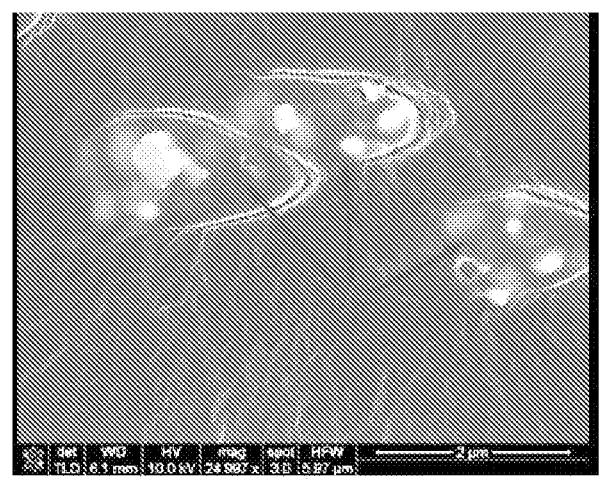
FIG. 2 is a SEM image of a composition containing an olefin-based polymer and an odor suppressant dispersed therein, in accordance with an embodiment of the present disclosure.

FIG. 1 is an SEM image of CS3 (5 wt % ZnO, D50=300 nm) blended in 95 wt % LLDPE (DOWLEX 2085G). FIG. 1 shows the ZnO particles dispersed in the LLDPE matrix phase. FIG. 2 is an SEM image of IE1 (5 wt % ZnO/5 wt % ZnI/O blended in 90 wt % LLDPE).

The SEM image of FIG. 2 shows the ZnI/O is a separate phase from the bulk LLDPE, and that the ZnO particles are encapsulated in the ZnI/O phase to form domains of ZnO embedded in the ZnI/O. Bounded by no particular theory, it is believed the formation of the ZnI/O—ZnO domains contributes to accelerated diffusion of odor molecules. The ZnI/O is more permeable to polar gasses (i.e., sulfur-based gasses, such as methyl mercaptan). The permeability of the ZnI/O facilitates the interaction of the odorous gas with the ZnO, contributing to the suppression of odor.

The SEM image of FIG. 2 shows that the ZnI/O surrounds, and encapsulates the ZnO particles. The ZnI/O prevents cavitation at the polymer-particle interface and prevents the rupture of the overall polymer. The ZnI/O—ZnO domains do not create initiation sites.

In Table 3, films CS1 through CS8 each exhibit a Dart impact strength less than 700 g whereas films IE1 and IE2 each exhibit Dart impact strength greater than 700 g and greater than 750 g (respective Dart impact values 810 g, 773 g).

Table 3 shows that the physical properties of Dart impact strength, for IE1 and IE2 are either maintained or improved when the present odor suppressant (ZnO and ZnI/O) is used compared to film containing ZnO alone. Indeed, IE1 and IE2 show improvement for all film properties (Dart impact, tear) compared to the unfilled film sample of control film CS1.

Applicant surprisingly discovered that the present odor suppressant (ZnO—ZnI/O) enables effective odor suppression using less total zinc utilizing ZnO particles with D50 100-3000 nm, surface area 1 m²/g-9 m²/g, and porosity less than 0.020 m³/g while simultaneously yielding blown film with improved Dart impact strength (i.e., Dart impact strength of 600 g and greater or 700 g and greater). The ability to improve odor suppression with less zinc by way of the present composition and odor suppressant while maintaining and improving film properties is unexpected.

It is specifically intended that the present disclosure not be limited to the embodiments and illustrations contained herein, but include modified forms of those embodiments including portions of the embodiments and combinations of elements of different embodiments as come within the scope of the following claims.

The invention claimed is:
1. A composition comprising:
(A) from 85 wt % to 99 wt % of an olefin-based polymer;
(B) from 15 wt % to 1 wt % of an odor suppressant comprising a blend of:
(i) particles of zinc oxide, the particles having a D50 particle size from 100 nm to 3000 nm, a surface area from 1 m²/g to 9 m²/g, and a porosity less than 0.020 m³/g;
(ii) a zinc ionomer, and
the composition has a methyl mercaptan odor suppression value of less than 70 at 3 days as measured in accordance with ASTM D5504-12.

2. The composition of claim 1, wherein the olefin-based polymer is an ethylene-based polymer to the exclusion of other polymers.

3. The composition of claim 2, wherein the ethylene-based polymer is linear low density polyethylene (LLDPE).

4. The composition of claim 1 wherein composition comprises from 0.1 wt % to 9 wt % zinc.

5. The composition of claim 4 wherein the zinc is present to the exclusion of Group 5 to Group 12 metals.

6. The composition of claim 1, wherein the weight % ratio between particles of zinc oxide (B)(i) to zinc ionomer (B)(ii) is from 3:1 to 1:7 based on total weight of the odor suppressant.

7. The composition of claim 6 wherein the weight % ratio between particles of zinc oxide (B)(i) to zinc ionomer (B)(ii) is from 1:3 to 1:7 based on total weight of the odor suppressant.

8. The composition of claim 7 wherein the odor suppressant is present in an amount from 1 wt % to 10 wt % based on total weight of the composition.

9. The composition of claim 1, wherein the particles of zinc oxide (B)(i) have a D50 particle size from 100 nm to 3000 nm;
a surface area from 1.0 $m^2/g$ to 5.0 $m^2/g$;
a porosity from 0.010 $m^3/g$ to 0.015 $m^3/g$; and
the composition has a methyl mercaptan odor suppression value of less than or equal to 55 at 3 days.

10. The composition of claim 9 wherein the composition comprises a continuous-phase composed of the ethylene-based polymer and a discontinuous-phase composed of domains of the zinc oxide particles (B)(i) embedded in the zinc ionomer (B)(ii).

11. The composition of claim 9 wherein the domains have an average diameter from 500 nm to 10,000 nm.

12. The composition of claim 1 wherein the zinc ionomer is a zinc salt of a polymer selected from the group of ethylene/methyl-methacrylic acid, ethylene/vinyl acrylic acid, ethylene/methacrylate, ethylene/n-butyl acrylic acid, and ethylene acrylic acid.

13. The composition of claim 1, wherein the zinc ionomer is a zinc salt of an ethylene/acrylic acid copolymer.

* * * * *